(12) United States Patent
Lambris et al.

(10) Patent No.: US 6,319,897 B1
(45) Date of Patent: Nov. 20, 2001

(54) PEPTIDES WHICH INHIBIT COMPLEMENT ACTIVATION

(76) Inventors: John D. Lambris, 36 Haymarket La.; Arvind K. Sahu, 275 S. Bryn Mawr Ave., Apt. 6, both of Bryn Mawr, PA (US) 19010

(*) Notice: Subject to any disclaimer, the term of this patent is extended or adjusted under 35 U.S.C. 154(b) by 0 days.

(21) Appl. No.: 09/142,680

(22) PCT Filed: Mar. 11, 1997

(86) PCT No.: PCT/US97/03756
§ 371 Date: Feb. 1, 1999
§ 102(e) Date: Feb. 1, 1999

(87) PCT Pub. No.: WO97/33603
PCT Pub. Date: Sep. 18, 1997

Related U.S. Application Data

(60) Provisional application No. 60/013,325, filed on Mar. 13, 1996.

(51) Int. Cl.[7] .......................... A61K 38/12; A61K 38/08; A61K 38/10; A61K 38/16; C07K 7/64
(52) U.S. Cl. .................................. 514/9; 514/12; 514/14; 514/15; 530/300; 530/317; 530/324; 530/327; 930/260
(58) Field of Search ...................... 530/327, 300, 530/317, 324; 514/9, 12, 14, 15; 930/260

(56) References Cited

U.S. PATENT DOCUMENTS 5,256,642   10/1993   Fearon et al. .............................. 514/8

OTHER PUBLICATIONS

Bowie et al. Deciphering the message in protein sequences: tolerance to amino acid substitutions. Science, (Mar. 16, 1990) 247 (4948) 1306–10.*

Ngo et al., in The Protein Folding Problem and Tertiary Structure Prediction, Merz and Le Grand (Eds), Aug. 1994, Springer Verlag, pp. 433 and 492–495.*

Kalli, K.R. et al., 1994, Therapeutic uses of recombinant protein inhibitors. Springer Semin. Immunopathol. 15:417–431.

Schasteen C.S. et al., 1991, Synthetic peptide inhibitors of complement serine proteases—III. Significant increase in inhibitor potency provides further support for the functional equivalence hypothesis. Molec. Immunol. 28:17–26.

Sahu et al., 1996, Inhibition of human complement by a C3–binding peptide isolated from a phage–displayed random peptide library. J. of Immunol. 157:884–891.

* cited by examiner

*Primary Examiner*—David Romeo
(74) *Attorney, Agent, or Firm*—Woodcock Washburn Kurtz Mackiewicz & Norris

(57) ABSTRACT

Peptides capable of inhibiting complement activation are provided. Methods of inhibiting complement activation and complement-mediated tissue injury using these peptides are also provided. In addition, a method of producing compositions capable of inhibiting complement activation using these peptides is provided, along with the peptide analogs and peptidomimetics produced by the method.

7 Claims, 7 Drawing Sheets

PEPTIDES WHICH INHIBIT COMPLEMENT ACTIVATION

This application claims the benefit of U.S. Provisional Application No. 60/013,325, filed Mar. 13, 1996, and International Application No. PCT/US97/03756 filed Mar. 11, 1997, the entire contents of which are incorporated by reference herein.

INTRODUCTION

This invention was made in the course of research sponsored by the National Institutes of Health. The U.S. Government may have certain rights in this invention.

BACKGROUND OF THE INVENTION

Complement is a group of related plasma proteins that participate in inflammatory reactions. The activation of complement by classical and alternative pathways generates kinins from platelets, eosinophils and neutrophils. This activation is important in phagocytosis and curtailing infection.

Although complement is an important line of defense against pathogenic organisms, its activation can also lead to host cell damage. Complement-mediated tissue injury has been reported in a wide variety of diseases, including autoimmune diseases such as experimental allergic neuritis (Vriesendorp et al. *J. Neuroimmunol.* 1995 58:157), type II collagen-induced arthritis (Watson, W. C. and A. S. Townes, *J. Exp. Med.* 1985 162:1878), myasthenia gravis (Nakano, S. and A. G. Engel, *Neurology* 1993 43:1167; Barohn, R. J. and R. L. Brey, *Clin. Neurol. Neurosurg.* 1993 95:285), hemolytic anemia (Schreiber, A. D. and M. M. Frank, *J. Clin. Invest.* 1972 51:575), glomerulonephritis (McLean, R. H. *Pediatr. Nephrol.* 1993 7:226), and immune complex-induced vasculitis (Cochrane, C. G. *Springer Semin. Immunopathol.* 1984 7:263). It has also been identified in the adult respiratory distress syndrome (Robbins et al. *Am. Rev. Respir. Dis.* 1987 135:651), stroke (Vasthare et al. *FASEB J.* 1993 7:A424), heart attack (Kilgore et al. *Cardiovasc. Res.* 1994 28:437), xenotransplantation (Wang et al. *Histochem . J.* 1992 24:102; Leventhal et al. *Transplantation* 1993 55:857), multiple sclerosis (Williams et al. *Clin. Neurosci.* 1994 2:229), burn injuries (Gallinaro et al. *Surg. Gynecol. Obstet.* 1992 174:435), extracorporeal dialysis and blood oxygenation (Pekna et al. *Clin. exp. Immunol.* 1993 91:404).

The third complement component, C3, is known to have an important role in both classical and alternative pathways of complement activation. Proteolytic activation of C3 by classical (C4b,2a) or alternative (C3b,Bb) pathway C3 convertase leads to cleavage of C3 into an anaphylotoxic peptide C3a and an opsonic fragment C3b. Covalent attachment of metastable C3b to target cells undergoing complement attack results in generation of C5a and formation of C5b–9 membrane attack complex. However, the tissue injury that results from complement activation is directly mediated by the membrane attack complex, C5b–C9, and indirectly by the generation of anaphylotoxic peptides C3a and C5a. These peptides induce damage through their effect on neutrophils and mast cells. Upon stimulation with C5a, neutrophils produce a serine elastase that causes tissue injury. C5a also triggers the generation of toxic oxygen-derived free radicals from neutrophils, and both C3a and C5a stimulate rapid and enhanced production of leukotrienes from IL-3-primed basophils.

Control of the activation process is mediated in vivo by a family of structurally and functionally related proteins termed regulators of complement activation (hereinafter referred to as RCA). The RCA include both plasma proteins, i.e. factor H and C4 binding protein (C4bp) and membrane proteins, i.e., complement receptor 1 (CR1), decay-accelerating factor (DAF) and membrane cofactor protein (MCP). These proteins inhibit the generation of C3a and C5a by inactivating the C3 and C5 convertases of the classical and alternative pathways. Inhibition of complement activation by these proteins is achieved by dissociation of the subunits of C3 and C5 convertases and/or by proteolytic inactivation of the subunits by factor I.

The importance of complement-mediated tissue injury via a wide variety of disease states underscores the growing need for a specific complement inhibitor. Various approaches have been used to identify such an inhibitor. These include targeting the serine proteases with peptides or chemical compounds. PCT/US95/02945 disclose chimeric complement inhibitor proteins having a first functional domain with C3 inhibitory activity and a second functional domain with C5b–9 inhibitory activity. More recently attempts have been made to target the thioester of C3. For example, salicyl hydroxamate, believed to be one of the most potent inhibitors of C3, inhibits complement by reacting with the thioester of C3 (Sim et al. *Biochem. J.* 1981 193:115). The 50% inhibitory concentrations required for the inhibition of classical and alternative pathway-mediated hemolytic activities with this compound were 280 μM and 33 μM, respectively. However, salicyl hydroxamate has been reported to produce systemic lupus erythematosus-like syndrome as a toxic side effect (Sim et al. *Lancet* 1984 ii:422). Kalli et al. demonstrated that a soluble form of CR1 (sCR1) suppresses complement in several complement-dependent disease models (*Springer Semin. Immunopathol.* 1994 15:417).

In the present invention, peptides that inhibit complement activation have been identified and synthesized.

SUMMARY OF THE INVENTION

An object of the present invention is to provide peptides and peptide analogs that inhibit complement activation. Exemplary peptides of the present invention comprise at least a portion of the amino acid sequence of the N-terminal cyclic region of a peptide of SEQ ID NO: 1. In a preferred embodiment, the peptides of the present invention comprise at least the 13 amino acid sequence of SEQ ID NO: 2.

Yet another object of the present invention is to provide a method of producing compositions, such as peptide analogs or peptidomimetics, capable of inhibiting complement activation which comprises identifying the conformation of a peptide having SEQ ID NO: 1 or SEQ ID NO: 2, which is capable of interacting with C3 to inhibit complement activation, and producing a composition having a sufficiently similar conformation so that the composition interacts with C3 to inhibit complement activation.

Yet another object of the present invention is to provide a composition having sufficiently similar conformation to the peptide having SEQ ID NO: 1 or SEQ ID NO: 2 such that the composition is capable of interacting with C3 to inhibit complement activation. Examples of such compositions include peptide analogs of SEQ ID NO: 1 or SEQ ID NO: 2, having conservative amino acid substitutions, i.e. substitutions that do not materially alter the structure of the analog as compared to SEQ ID NOS: 1 or 2, and having complement-inhibiting activity. Other examples include peptidomimetics having sufficiently similar conformation to SEQ ID NOS: 1 or 2 so as to exhibit complement-inhibiting activity.

Another object of the present invention is to provide a method of inhibiting complement activation in a patient comprising administering to a human an effective amount of a peptide of the present invention.

Yet another object of the present invention is to provide a method treating complement-mediated tissue injury in a patient comprising administering to a patient an effective amount of a peptide of the present invention.

Yet another object of the present invention is to provide a method of inhibiting complement activation which occurs during use of artificial organs or implants which comprises coating the artificial organ or implant with a peptide of the present invention.

Yet another object of the present invention is to provide a method of inhibiting complement activation that occurs during extracorporeal shunting of physiological fluids (e.g. blood, urine), which comprises coating the tubing through which said fluids are shunted with a peptide of the present invention.

DETAILED DESCRIPTION OF INVENTION

Peptides that inhibit complement activation have now been identified. The peptides of the present invention comprise at least a portion of the N-terminal cyclic region of a peptide of SEQ ID NO: 1. In a preferred embodiment, the peptides of the present invention comprise at least the 13 amino acid sequence of SEQ ID NO: 2. Analogs and mimetics of SEQ ID NO: 1 and SEQ ID NO: 2 are also within the scope of this invention.

To identify peptides of the present invention, a phage-displayed random peptide library containing 2×10$^8$ unique clones expressing random peptides 27 amino acids in length was screened. Peptides of this library are fused to the amino terminus of the mature protein III of bacteriophage M13. Because C3b has a relatively low affinity for other complement proteins, half-physiologic ionic strength buffers have traditionally been used to study these interactions. However, to increase the probability of selecting a phage with high affinity, buffers of physiologic ionic strength for biopanning were used. Phage particles expressing C3b-binding peptides were affinity-purified by plating on a microtiter plate coated with C3b. After a third round of biopanning, individual phage were isolated and tested for binding; 14 of 16 clones bound to C3b. DNA was isolated from all positive clones and the nucleotide sequence of each was determined. All fourteen positive clones had an identical sequence, indicating that this clone was specific and had been amplified during the second and third rounds of biopanning.

Figure 1:
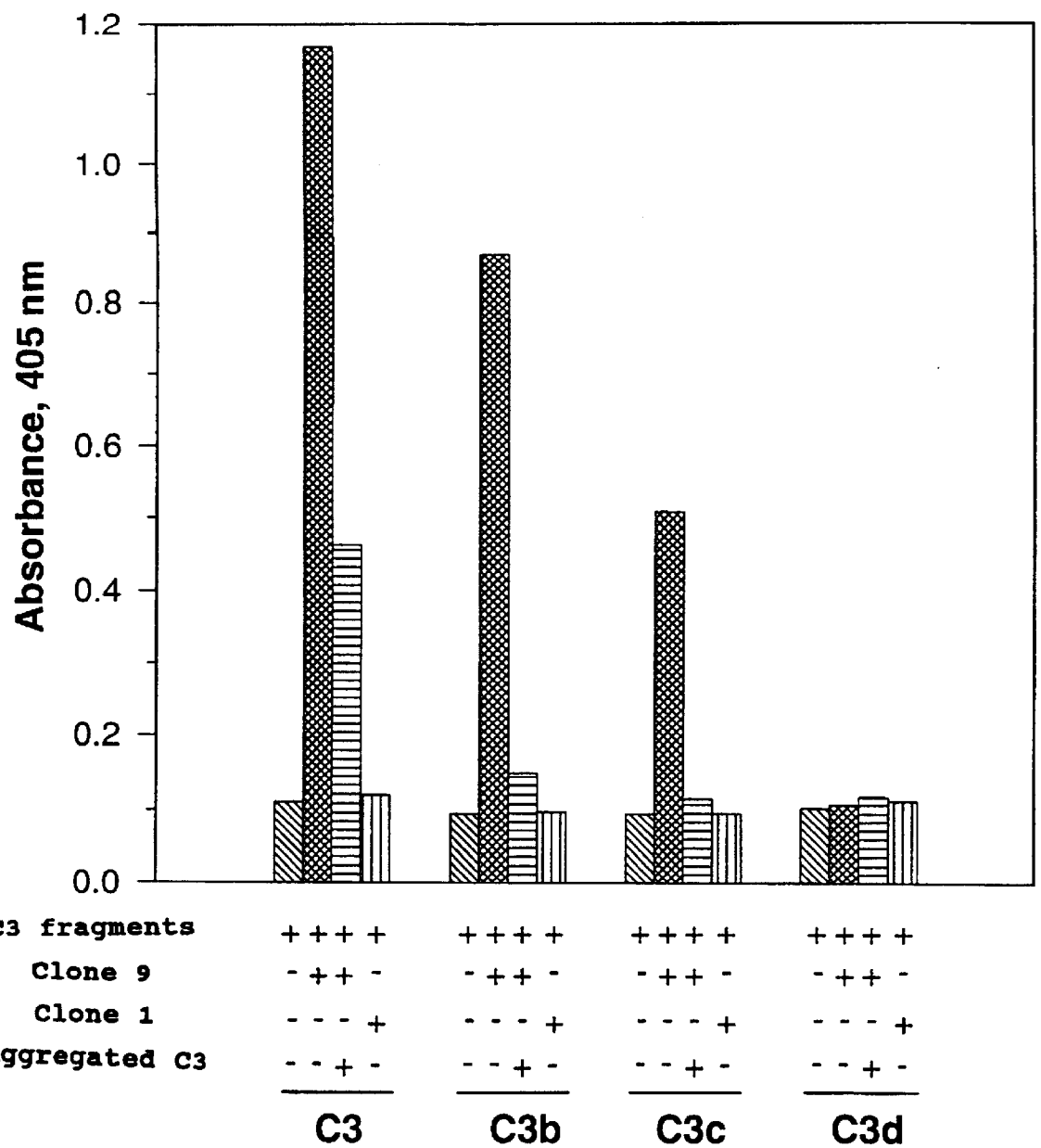
FIG. 1 is a bargraph showing specific binding of a C3 binding clone isolated from a phage-displayed random peptide library to C3 and C3 fragments including: C3b, the proteolytically activated form of C3; C3c, 135,300 Mr fragment of C3 generated using elastase; and C3d, 35,000 Mr fragment of C3 generated using elastase. Microtiter wells were coated with 2 μg of C3, C3b, C3c or C3d, saturated with blocking buffer, washed with PBS (pH 7.4) containing 0.05% Tween 20, and incubated 1 hour at 22° C. with a positive (clone 9) or negative (clone 1) clone. Binding was inhibited by adding 250 μg/ml of aggregated C3 in PBS, pH 7.4. Bound M13 phage particles were detected by peroxidase-coupled anti-M13 antibody and ABTS peroxidase substrate. Diagonally lined bars represent peroxidase-coupled anti-M13 antibody bound non-specifically to the plate; cross-hatched bars represent clone 9 bound to C3 or C3 fragments; horizontally lined bars represent clone 9 bound to C3 or C3 fragments in the presence of 250 μg/ml of aggregated C3; and vertically lined bars represent clone 1 bound to C3 or C3 fragments.

Binding results obtained with representative positive (clone 9; SEQ ID NO: 4) and negative (clone 1) clones showed that clone 9 bound to immobilized C3, C3b and C3c but not to C3d (see FIG. 1). The binding strength of the positive clone followed the order C3>C3b>C3c. Specificity of the binding of clone 9 was demonstrated by ELISA. Aggregated C3 (250 μg/ml) significantly inhibited the binding to C3, C3b and C3c.

Figure 2:
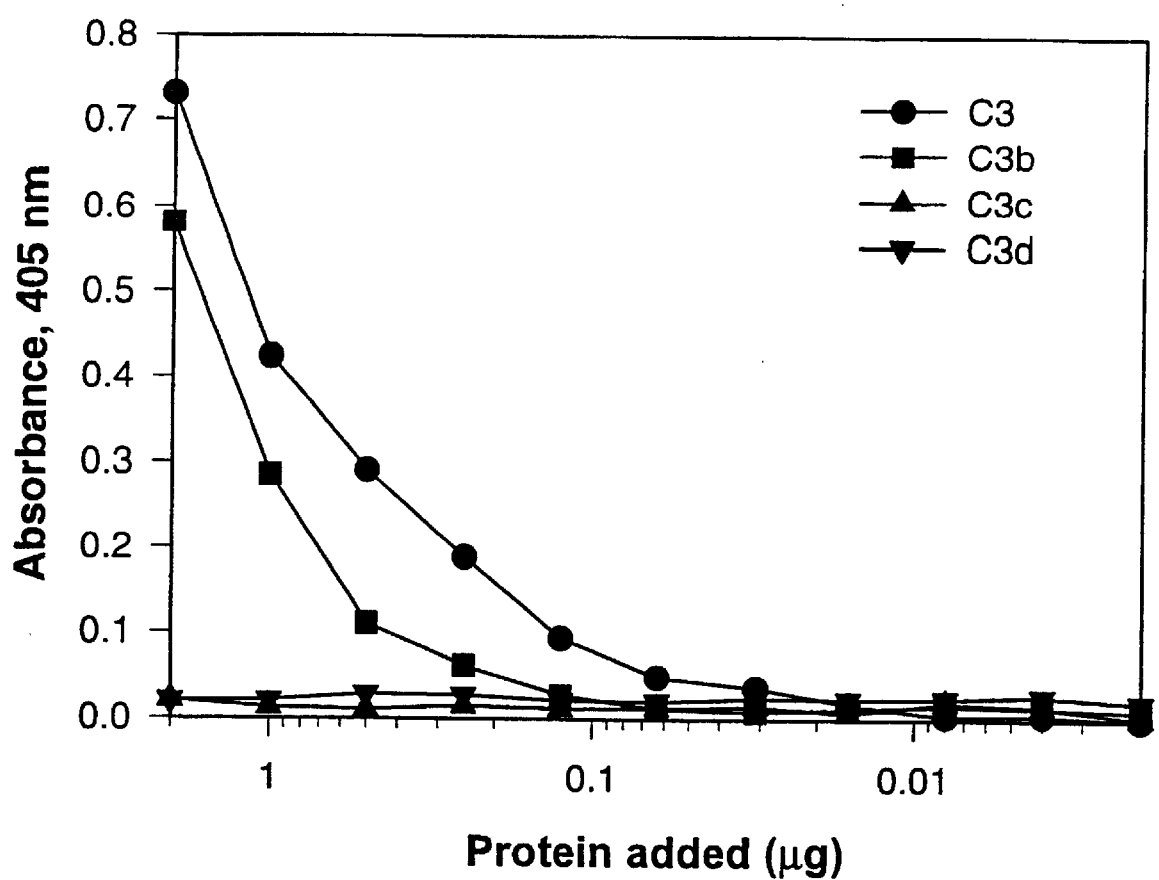
FIG. 2 is a linegraph showing the binding of peptide I to C3 and C3 fragments. A microtiter plate was coated with peptide I, saturated with blocking buffer, washed with PBS (pH 7.4) containing 0.05% Tween 20, and incubated with two-fold dilutions of C3 (●), C3b (■), C3c (▲) or C3d (▼) for 1 hour at 22° C. The plate was then washed and incubated with a polyclonal rabbit anti-C3 antibody (2 μg/ml) and a 1:1000 dilution of peroxidase-coupled anti-rabbit antibody. Color was developed with the ABTS peroxidase substrate.

A 27-amino acid peptide (SEQ ID NO: 1) corresponding to the phage-displayed peptide was synthesized. This peptide, in its cyclic form, is referred to herein as peptide I. The amino acid sequence of peptide I is shown in Table 1. Peptide I was found to bind to C3 and some C3 fragments, inhibiting both classical and alternative pathways of complement activation. The synthetic peptide (peptide I) was coated on a microtiter plate and its binding to C3 and C3 fragments was analyzed by ELISA. Immobilized peptide I bound to C3 and C3b; however, no binding to C3d was detected (FIG. 2). Peptide I also did not bind to C3c (FIG. 2), thus indicating that the peptide's binding site is buried when C3c is present in its native conformation.

Figure 3A:
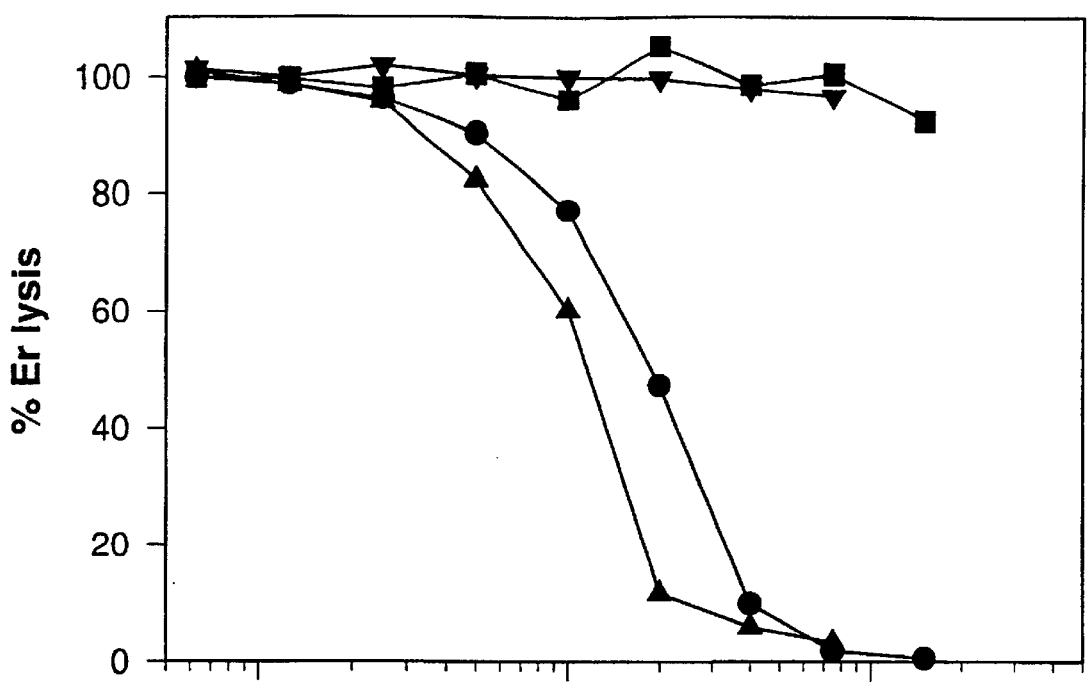
FIG. 3 is a linegraph showing inhibition of classical and alternative pathway-mediated lysis of erythrocytes by peptides of the present invention. Cyclic peptides (peptide I (●) and peptide IV (▲)) and reduced and alkylated peptides (peptide II (■) and V (▼)) were tested for their effect on the alternative (panel A) and classical (panel B) pathways of complement activation.
Figure 3B:
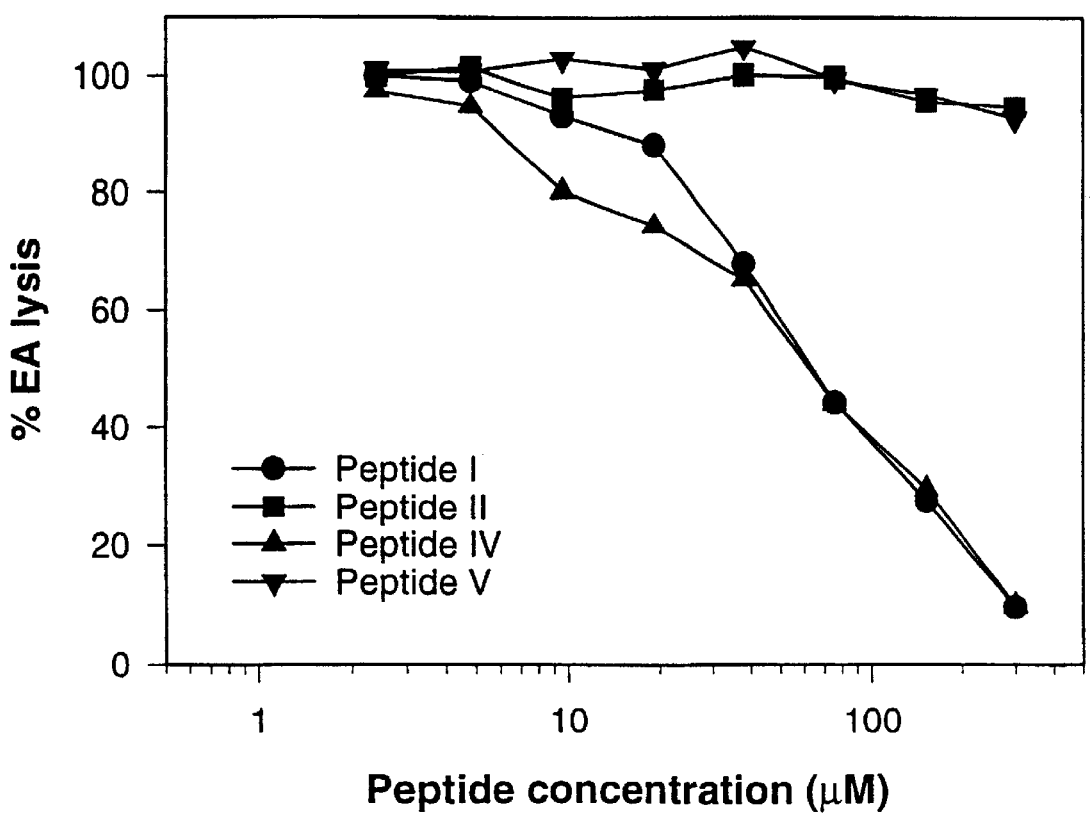

This peptide inhibits complement activation in normal human serum by inhibiting the proteolytic activation of C3 at a concentration approximately twice that of human C3. Inhibition of the alternative pathway was measured by using rabbit erythrocytes in the presence of MgEGTA (FIG. 3A); inhibition of lysis of antibody-coated sheep erythrocytes was used as an indicator of inhibition of the classical pathway (FIG. 3B). Peptide I inhibited both classical and alternative pathways with $IC_{50}$ of 65 μM and 19 μM, respectively.

Analysis of the mechanism of inhibition revealed that this peptide inhibited C3 cleavage in normal human serum in the presence of MgEGTA. Similar results were obtained when the alternative pathway was reconstituted with purified complement components. However, the peptide did not inhibit the cleavage of factor B, indicating that it did not affect the interaction of C3b with factor B or the formation of C3b,Bb. The peptide also had no effect on the binding of properdin to C3, demonstrating that the observed inhibition of C3 cleavage in normal human serum was not due in part to its effect on the properdin-stabilized C3 convertase, C3b,Bb,P. These results indicate that, unlike other regulators of complement activation (factor H, MCP, DAF and CR1) that inhibit the activation process subsequent to the generation of C3b, the peptide of the present invention interacts directly with native C3 to inhibit its activation.

Various analogs of peptide I were examined to the determine the region or residues of the peptide involved in inhibition of complement. Results from these experiments are shown in Table 1. The purity and identity of all the peptides were critically monitored by laser desorption mass spectrometry (Moore, W. T. *Biol. Mass Spectrom.* 1993 22:149–162). In all cyclic peptides, formation of a disulfide bond was confirmed mass spectrometrically using a mass shift assay involving reactions of thiols with p-hydroxy mercuribenzoic acid (Angeletti et al. *Techniques in Protein Chemistry VII*. Edited by Marshak DR. San Diego, Academic Press, 1996 p. 261).

TABLE I

AMINO ACID SEQUENCES AND FUNCTIONAL ACTIVITY OF
C3 BINDING PEPTIDE AND ITS ANALOGS

| PEPTIDE/ CLONE | AMINO ACID SEQUENCE | CLASSICAL PATHWAY $IC_{50}$ (μM) | ALTERNATIVE PATHWAY $IC_{50}$ (μM) |
|---|---|---|---|
| CLONE 9 SEQ ID NO: 4 | SSICVVQDWGHHRCTAGHMANLTSHASAIR | N.D. | N.D. |
| PEPTIDE I SEQ ID NO: 1 | ICVVQDWGHHRCTAGHMANLTSHASAI (cyclic) | 65 | 19 |
| PEPTIDE II SEQ ID NO: 1 | ICVVQDWGHHRCTAGHMANLTSHASAI | >300 | >300 |
| PEPTIDE III SEQ ID NO: 3 | RATAGHMANLTSHASAI | >300 | >300 |
| PEPTIDE IV SEQ ID NO: 2 | ICVVQDWGHHRCT (cyclic) | 63 | 12 |
| PEPTIDE V SEQ ID NO: 2 | ICVVQDWGHHRCT | >600 | >300 |
| PEPTIDE VI SEQ ID NO: 13 | CVVQDWGHHRC (cyclic) | N.D. | 33 |
| PEPTIDE VII SEQ ID NO: 5 | CHHRCT (cyclic) | N.D. | >600 |
| PEPTIDE VIII SEQ ID NO: 6 | CGHHRCT (cyclic) | N.D. | >600 |

TABLE I-continued

AMINO ACID SEQUENCES AND FUNCTIONAL ACTIVITY OF C3 BINDING PEPTIDE AND ITS ANALOGS

| PEPTIDE/ CLONE | AMINO ACID SEQUENCE | CLASSICAL PATHWAY IC$_{50}$ ($\mu$M) | ALTERNATIVE PATHWAY IC$_{50}$ ($\mu$M) |
|---|---|---|---|
| PEPTIDE IX SEQ ID NO: 7 | CWGHHRCT | N.D. | >600 |
| PEPTIDE X SEQ ID NO: 8 | CDWGHHRCT | N.D. | >600 |
| PEPTIDE XI SEQ ID NO: 9 | CQDWGHHRCT | N.D. | >600 |
| PEPTIDE XII SEQ ID NO: 10 | CVQDWGHHRCT | N.D. | >600 |
| PEPTIDE XIII SEQ ID NO: 11 | CVVQDWC | N.D. | >600 |
| PEPTIDE XIV SEQ ID NO: 12 | CVVQDWGHC | N.D. | >600 |
| PEPTIDE XV SEQ ID NO: 14 | CAVQDWGHHRC | N.D. | 1200 |
| PEPTIDE XVI SEQ ID NO: 15 | CVAQDWGHHRC | N.D. | 67 |
| PEPTIDE XVII SEQ ID NO: 16 | CVVADWGHHRC | N.D. | 910 |
| PEPTIDE XVIII SEQ ID NO: 17 | CVVQAWGHHRC | N.D. | 257 |
| PEPTIDE XIX SEQ ID NO: 18 | CVVQDAGHHRC | N.D. | 182 |
| PEPTIDE XX SEQ ID NO: 19 | CVVQDWAHHRC | N.D. | >1200 |
| PEPTIDE XXI SEQ ID NO: 20 | CVVQDWGAHRC | N.D. | 15 |
| PEPTIDE XXII SEQ ID NO: 21 | CVVQDWGHARC | N.D. | 74 |
| PEPTIDE XXIII SEQ ID NO: 22 | CVVQDWGHHAC | N.D. | 70 |

(N.D. = not done)

To identify the minimal region of peptide I that is required for interaction with C3, two overlapping peptides were synthesized and their activities determined in the classical and alternative pathway-mediated hemolytic assays. See Table 1. The two overlapping peptides tested were the cyclic 13-amino acid N-terminal peptide (peptide IV) and the linear 17-mer C terminal peptide (peptide III). Inhibitory activity was retained by the cyclic N-terminal region of the parent peptide (peptide IV). In contrast, peptide III showed no inhibitory activity, indicating that this region is not important for binding. In addition, linear peptides II and V were made by reducing and alkylating peptide I and IV, respectively. This reduction and alkylation destroyed the inhibitory activity of peptides I and IV, indicating that the cysteine disulfide bridge is important in maintaining the stable structure of peptide I and IV. The concentration of peptide I or IV that was required to inhibit the alternative pathway was lower than that required to inhibit the classical pathway, perhaps because the alternative pathway is more sensitive to activation and deposition of C3 on the target cells.

Peptide IV contains two flanking amino acid residues outside the constrained region. To further reduce the size of the peptide, these two residues were deleted to produce peptide VI. This deletion resulted in approximately 2.8-fold reduction in the activity of the peptide, thus indicating the importance of these residues in enhancing the inhibitory activity of the peptide.

An additional series of analogs was synthesized in order to localize the minimal functional region of the peptide. Short constrained peptides were generated by changing the ring size. For this purpose, one to six residues inside the 11-membered ring were deleted (peptides VII–XIV of Table 1). However, activity was lost in all the peptides of this series, indicating that the full length 11-membered ring is important for biological activity.

In an additional series of analogs, the contribution of each residue to maintaining biological activity of the peptide was determined by replacing it with an Ala. In this series of nine peptides (peptide XV–XXIII of Table 1), each residue of the 11-membered ring, except for the two cysteines, was systematically substituted with alanine. Replacement of $Val^3$, $His^9$ or $Arg^{10}$ resulted in minimal change in the functional activity, suggesting that these residues may not contribute significantly to the interaction C3b. Replacement of $Val^2$, $Gln^4$, $Asp^5$ or $Trp^6$ reduced the activity of the peptide from 6- to 36-fold as compared to peptide VI. These residues are clustered together in the N-terminal half of the peptide. Replacement of $Gly^7$ with Ala dramatically reduced the activity of the peptide by more than 100-fold, suggesting that the side chain of the Ala may sterically hinder the binding of the peptide to C3, or that the free rotation around glycine is important for binding. Thus, it is believed that the side chains of $Val^2$, $Gln^4$, $Asp^5$ and Trp6 contribute significantly to the binding and biological activity of the peptide.

Figure 4:
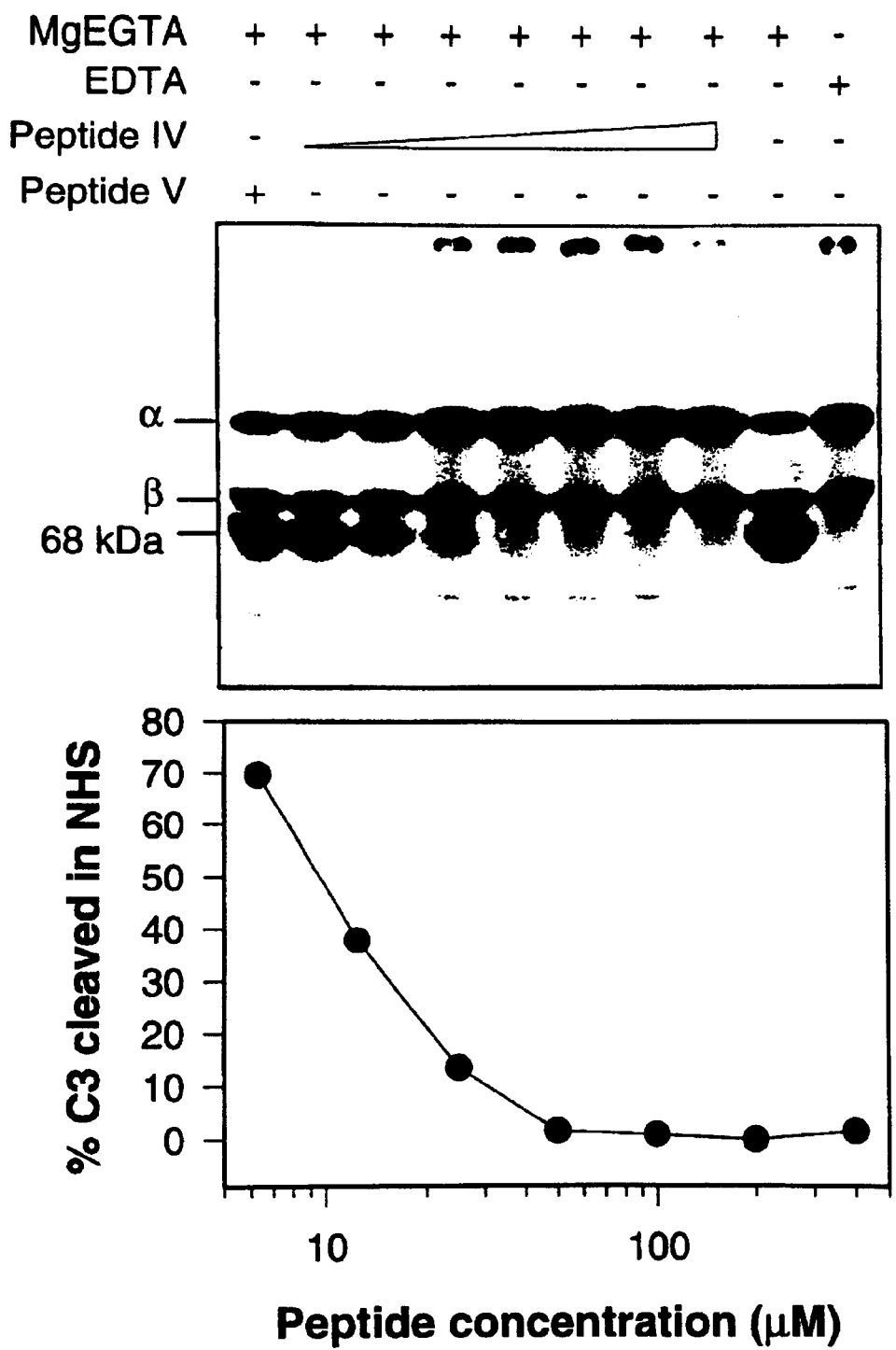
FIG. 4 shows inhibition of C3 cleavage by peptide IV during alternative pathway activation in normal human serum (hereinafter referred to as NHS). Cleavage of C3 was measured by incubating NHS containing $^{125}$I-C3 (0.5 μCi) with 5 mM MgEGTA, zymosan, and increasing concentrations of peptide IV for 30 minutes at 37° C. Samples were run on 7.5% SDS-PAGE under reducing conditions and the gel was subjected to autoradiography. Radioactive bands were cut out and counted. The data were normalized by considering 100% cleavage of C3 to be equal to the amount of C3 cleaved in the absence of peptide IV. Controls contained 10 mM EDTA. The reduced and alkylated peptide V (200 μM) was included as a control peptide.

Peptide IV has also determined to inhibit C3 convertase C3b,Bb-mediated cleavage of C3 in a concentration dependent manner (see FIG. 4). The peptide inhibited C3 cleavage with an $IC_{50}$ of 10 $\mu$M that correlated well with the concentration required to inhibit 50% of the hemolytic activity (Table 1). During complement activation in serum, C3 convertase cleaves C3 into C3b, which is immediately inactivated by factors H and I to iC3b. This assay measures the amount of iC3b generated during activation. Thus, to verify that the measured inhibition was due to inhibition of C3 cleavage by C3 convertase and not to inhibition of factors H- and I-mediated cleavage of C3b to iC3b, 5 $\mu$g of purified C3b was incubated with 1 $\mu$g of factor H and 0.04 $\mu$g of factor I in the presence of peptide IV. No inhibition of iC3b generation was observed, even at 300 $\mu$M, a concentration 30 times higher than the $IC_{50}$ for C3 cleavage.

Figure 5:
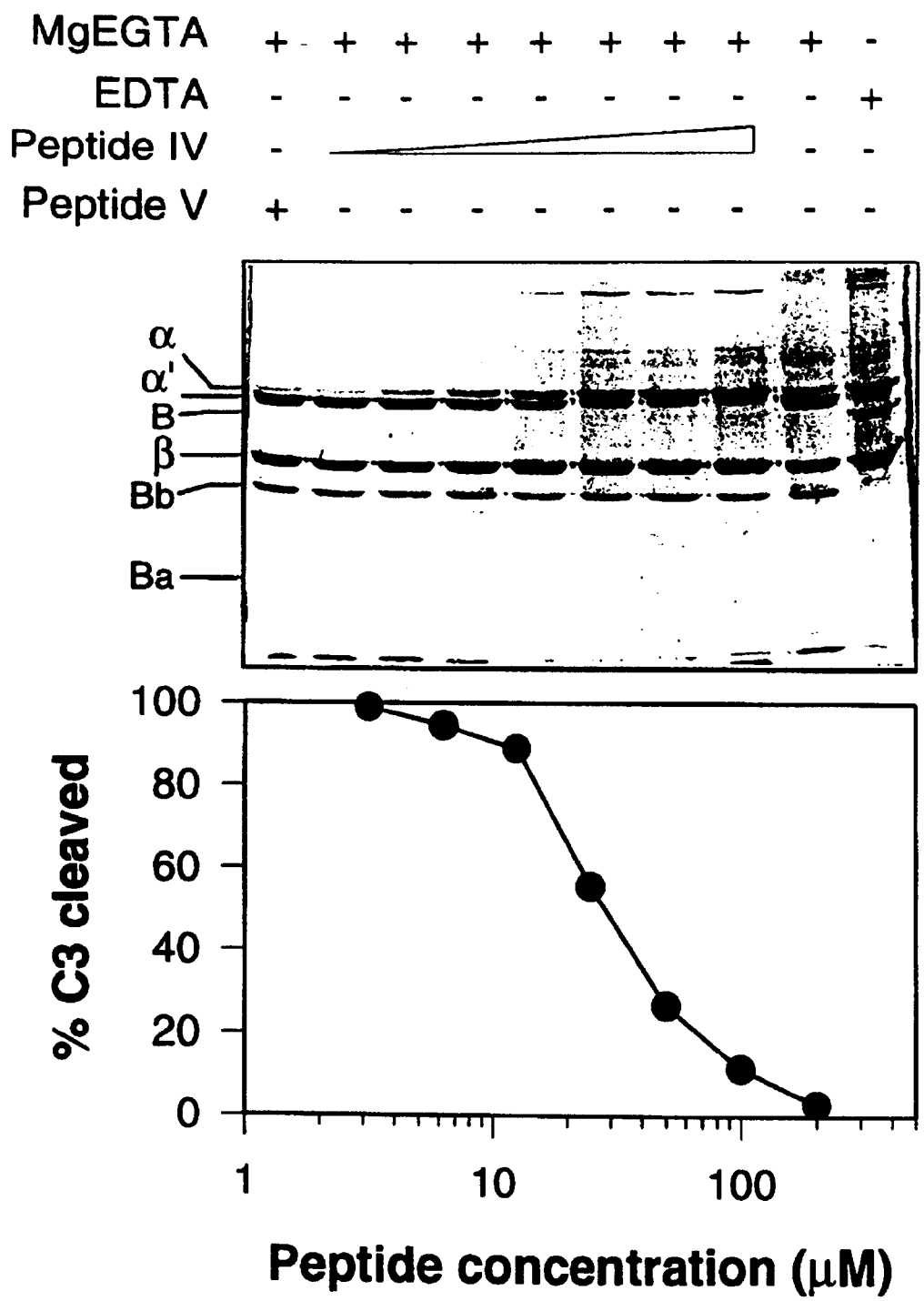
FIG. 5 shows inhibition of C3 cleavage by peptide IV during activation of the alternative pathway reconstituted with purified components. The alternative pathway was reconstituted by adding C3 and factors B and D, and various concentrations of the peptide IV were added. Samples were analyzed by running on 7.5% SDS-PAGE under reducing conditions. The gel was stained with Coomassie Blue and the intensity of each band was determined by densitometric analysis. Data were normalized by considering 100% cleavage of C3 to be equal to the cleavage observed in the absence of peptide IV. Controls contained EDTA. The reduced and alkylated peptide V (200 μM) was included as a control peptide.
Figure 6:
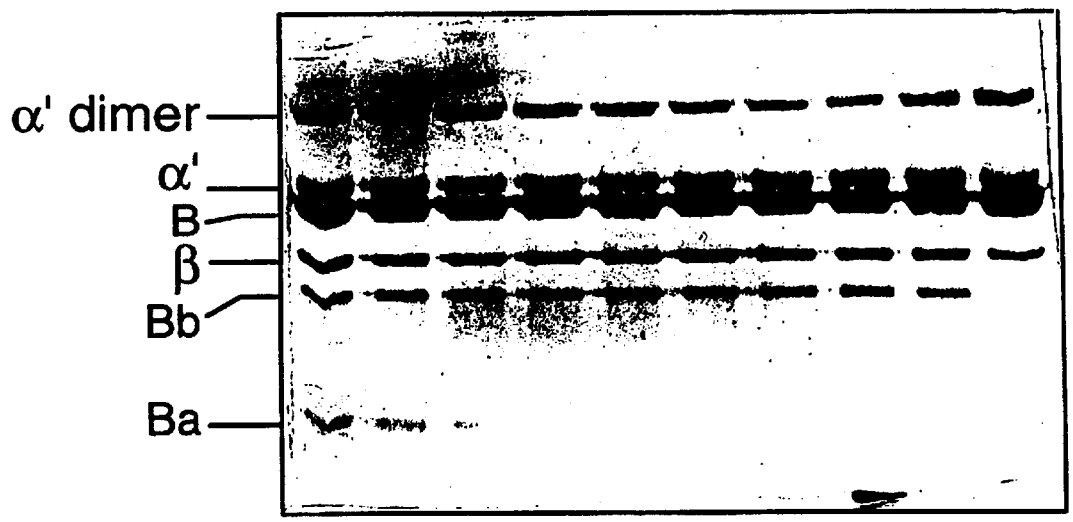
FIG. 6 shows the effect of peptide IV on factor B cleavage. Factor B cleavage was quantitated by incubating C3b with factor B, factor D and various concentrations of peptide IV (6 μM–400 μM) in the presence of MgEGTA for 1 hour at 37° C. Samples were analyzed on 7.5% SDS-PAGE in the presence of DTT. The gel was stained and scanned for densitometric analysis. The reduced and alkylated peptide v (200 μM) was included as a control peptide. Controls were set by adding 10 mM EDTA.

To examine the effect of peptide IV on purified C3, free of possible labeling artifacts, the alternative pathway was reconstituted with purified C3, factor B and factor D (see FIG. 5). Peptide IV inhibited the proteolytic activation of C3 to C3b, with an $IC_{50}$ of 28 $\mu$M. Peptide V, the reduced and alkylated form of peptide IV, had no effect on C3 cleavage. The interaction of C3b with factor B in a fluid phase assay in which purified C3b, factor B and factor D were incubated together with MgEGTA so as to generate C3b,Bb in the presence or absence of peptide IV was also determined. The concentration of factor D was adjusted to generate limited cleavage of factor B. Peptide IV showed no inhibition of factor B cleavage (FIG. 6), indicating that this peptide has no effect on the interaction of C3b with factor B or on C3b,Bb formation.

Figure 7:
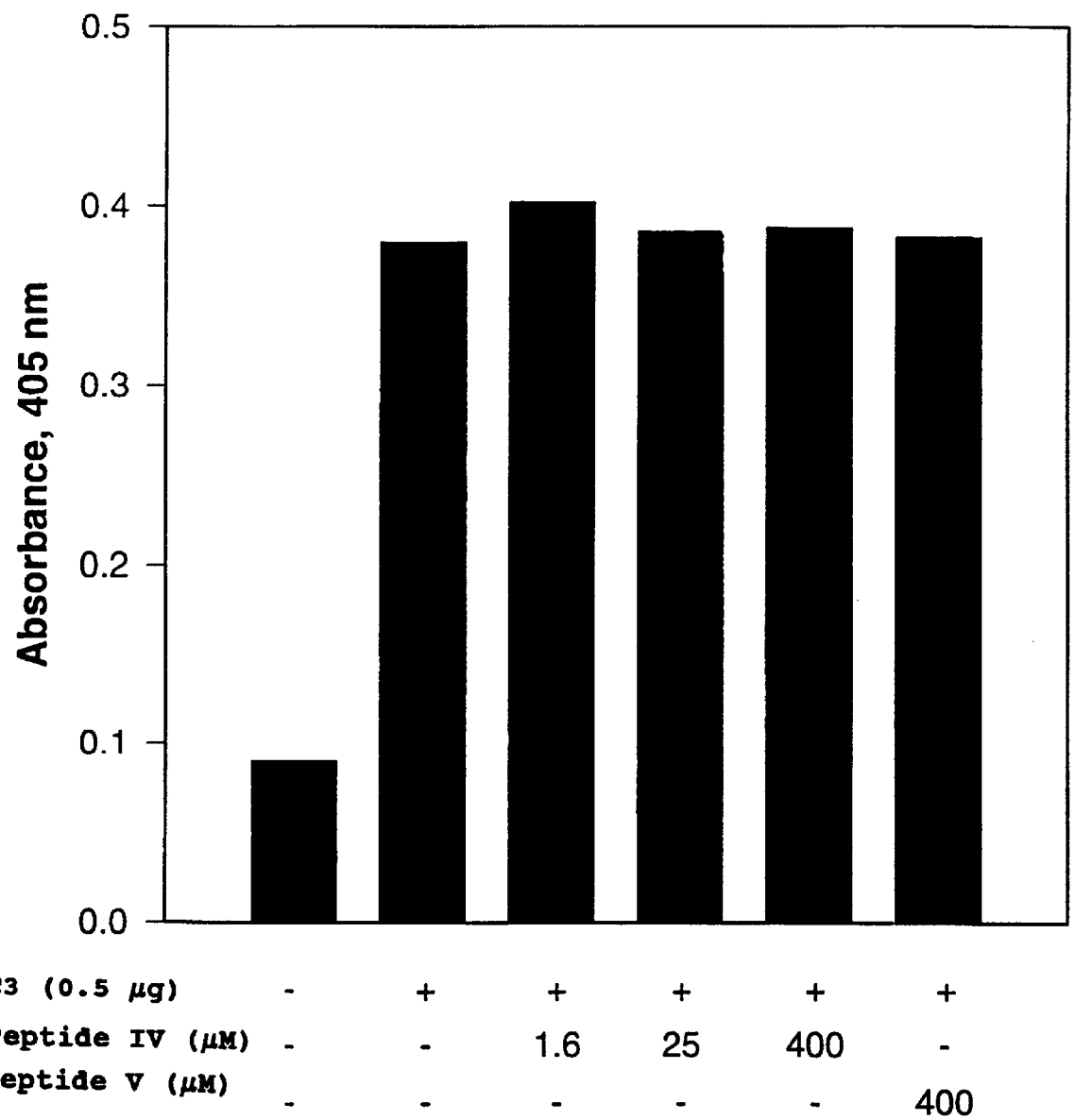
FIG. 7 is a bargraph showing the effect of peptide IV on properdin binding to C3 coated to a microtiter plate. C3 (20 μg/ml) was coated onto microtiter wells and incubated with NHS containing 10 mM EDTA and graded concentrations of peptide IV for 1 hour at 22° C. Binding of properdin was detected by a polyclonal goat anti-properdin antibody (10 Ag/ml) and a 1:1000 dilution of peroxidase-conjugated anti-goat antibody. The reduced and alkylated peptide V was included as a control peptide.

The effect of peptide IV on properdin binding to C3 was also determined using a competitive ELISA (see FIG. 7). Peptide IV had no significant effect on properdin binding to C3, indicating that the observed inhibition of C3 cleavage in NHS is not due to disruption of the properdin-stabilized C3 convertase, c3b,Bb,P.

The proteolytically activated form of C3, C3b, binds to more than 20 serum and membrane proteins, most of which belong to a superfamily of structurally and functionally related molecules. However, in native C3 the binding sites for these proteins are buried and become available only after the conformational change that occurs upon the cleavage of C3 to C3b. The data presented in FIGS. 1, 2, and 5 makes it clear that peptides I and IV bind to native C3 and inhibit its activation. Thus, the inhibition of complement with these inhibitory peptides not only inhibits the generation of C5a but also of C3a.

Synthetic peptides of the present invention which are analogous to the identified phage-displayed C3-binding peptide were able to inhibit the alternative pathway of complement activation at a concentration that was only two-fold greater than the concentration of C3 in NHS (FIG. 3 and Table 1). The concentration required to inhibit the classical pathway was 5-fold higher than that required to inhibit the alternative pathway thus indicating that the inhibitory action of the peptides of the present invention is probably directed toward the activation of C3 or C3 convertase. Accordingly, the peptides of the present invention are believed to be useful as therapeutics in diseases involving complement-mediated damage. Examples of complement-mediated diseases include, but are not limited to, autoimmune diseases such as experimental allergic neuritis, type II collagen-induced arthritis, myasthenia gravis, hemolytic anemia, glomerulonephritis, and immune complex-induced vasculitis, adult respiratory distress syndrome, stroke, heart attack, xenotransplantation, multiple sclerosis, burn injuries, extracorporeal dialysis and blood oxygenation. Thus, in the present invention, patients suffering from a disease involving complement-mediated damage can be administered an effective amount of a peptide of the invention so that complement activation is inhibited. By "effective amount" it is meant a concentration of peptide which is capable of inhibiting complement activation. Such concentrations can be routinely determined based upon in vitro data such as that provided herein. Appropriate modes of administration, dose ranges and pharmaceutical vehicles can also be routinely determined by those of skill in the art in accordance with the disease to be treated and the patient profile.

The compositions of the present invention will also find use in other situations in which inhibition of complement activation is desired. For instance, complement activation that occurs in xerographic or allographic transplant may be inhibited by administering a peptide of the invention to a patient receiving such transplant, or by coating organs with a peptide of the invention. Further, the peptides of the present invention can be used to coat biomaterials used in artificial organs and implants to inhibit complement activation which occurs during use of these artificial materials. As another example, complement activation during extracorporeal shunting of physiologic fluid may be inhibited by coating tubing through which the fluids flow with a peptide of the invention. This method can be applied to a variety of extracorporeal shunting techniques, including hemodialysis, kidney dialysis and cardiopulmonary bypass circuits.

The inhibitory activity of peptides I and IV is highly specific to human C3. Peptides I and IV had no inhibitory activity on the complement mediated lysis of rabbit erythrocytes by mouse or rat complement. Further, studies with these peptides in C3-knockout mice wherein hemolytic activity is reconstituted with human C3 showed inhibition at concentrations similar to those seen for human serum. Accordingly, initial testing of in vivo effectiveness of these peptides in various disease models would need to be performed in models such as transgenic mice expressing human C3 or alternatively, C3 knockout mice infused with human C3. The inhibitory activity of peptide IV on guinea pig, swine and monkey complement was also determined. The peptide inhibited monkey complement but failed to inhibit guinea pig or swine complement. Complement inhibition in Rhesus monkeys, cynomolgus monkeys and baboons was comparable to that in humans.

The rate of clearance of a protein or peptide is an important determinant of its biological effects. Accordingly, the in vivo half-life of a peptide of the present invention was determined in SJL mice. A peptide of the invention containing tyrosine residues at its C-terminus (ICVVQDWGHHRCTAGHYY (SEQ ID NO: 23)) which demonstrated equal activity to Peptide IV in a hemolytic assay was used. This peptide showed a heterogeneous clearance rate, with a $t_{1/2}$ of 11 hours.

Due to the specificity for C3 and effectiveness of the peptides of the present invention, they can also be used as reagents to inhibit C3 activation in vitro assay systems. In addition, the specificity of these peptides to C3 makes them very useful in further elucidating the importance of different components in the complement cascade.

Peptides of the present invention, especially SEQ ID NO: 1 and SEQ ID NO: 2, are also useful to identify specific conformational features required for the peptide to interact with C3 and inhibit complement activation. One example of a structure-function analysis is described in Example 12. That study employed a retro-inverso peptidomimetic of a peptide of the invention to reveal the relative importance of main chain versus side-chain amino acid configurations in the complement-inhibitory activity of the peptide.

Other standard approaches to determine the structures of peptides of the invention can also be used. These include a variety of nuclear magnetic resonance techniques, combined with various computational methods.

Using such standard approaches, compositions having sufficiently similar conformations can be produced and tested for their ability to inhibit complement activation. By "sufficiently similar" it is meant a conformation which is capable of interacting with C3 and inhibiting complement activation. Further, C3 knockout mice or mice expressing human C3 can be used in studying structure/function relationships of human C3, either by blocking specific function with anti-C3 monoclonal antibodies or by infusing mutant forms of C3.

Once a particular desired conformation of a short peptide has been ascertained, methods for designing a peptide or peptidomimetic to fit that conformation are well known in the art. See, e.g., G. R. Marshall (1993), Tetrahedron, 49: 3547–3558; Hruby and Nikiforovich (1991), in *Molecular Conformation and Biological Interactions*, P. Balaram & S. Ramasehan, eds., Indian Acad. of Sci., Bangalore, PP. 429–455). The design of peptide analogs may be further refined by considering the contribution of various side chains of amino acid residues, as discussed above (i.e., for the effect of functional groups or for steric considerations).

It will be appreciated by those of skill in the art that a peptide mimic may serve equally well as a peptide for the purpose of providing the specific backbone conformation and side chain functionalities required for binding to C3 and inhibiting complement activation. Accordingly, it is contemplated as being within the scope of the present invention to produce C3-binding, complement-inhibiting compounds through the use of either naturally-occurring amino acids, amino acid derivatives, analogs or non-amino acid molecules capable of being joined to form the appropriate backbone conformation. A non-peptide analog, or an analog comprising peptide and non-peptide components, is sometimes referred to herein as a "peptidomimetic", to designate substitutions or derivations of the peptides of the invention, which possess the same backbone conformational features and/or other functionalities, so as to be sufficiently similar to the exemplified peptides to inhibit complement activation.

The use of peptidomimetics for the development of high-affinity peptide analogs is well known in the art (see, e.g., Zhao et al. (1995), Nature Structural Biology 2: 1131–1137; Beely, N. (1994), Trends in Biotechnology 12: 213–216; Hruby, V. J. (1993), Biopolymers 33: 1073–1082). Assuming rotational constraints similar to those of amino acid residues within a peptide, analogs comprising non-amino acid moieties may be analyzed, and their conformational motifs verified, by means of the Ramachandran plot (see Hruby & Nikiforovich, supra), among other known techniques.

The following nonlimiting examples are provided to further illustrate the present invention.

EXAMPLES

Example 1

Chemicals and Buffers

All chemicals and reagents used for peptide synthesis were purchased from Applied Biosystems (Foster City, Calif.), with the exception of Fmoc amino acids, which were obtained from Nova Biochem (San Diego, Calif.). Veronal-buffered saline (VBS), pH 7.4, contained 5 mM barbital and 145 mM NaCl. Gelatin veronal-buffered saline (GVB) was VBS containing 0.1% gelatin, GVB++ was GVB containing 0.5 mM $MgCl_2$ and 0.15 mM $CaCl_2$, and GVBE was GVB with 10 mM EDTA. MgEGTA, contained 0.1 M $MgCl_2$ and 0.1 M EGTA. Phosphate-buffered saline (PBS), pH 7.4, contained 10 mM phosphate and 145 mM NaCl. Blocking buffer was PBS containing 0.5% milk and 1% bovine serum albumin (BSA).

Example 2

Purified Complement Components

Human complement proteins C3, factor B, factor H and factor I were purified from normal human plasma in accordance with well known procedures. The C3 used in these experiments was a mixture of 72% native C3 and 28% $C3(H_2O)$, as determined by analyzing a sample of the protein on a Mono S column (Pharmacia, Piscataway, N.J.) in accordance with procedures described by Pangburn, M. K. *J. Immunol. Methods* 1987 102:7. C3b was generated by limited trypsin cleavage of C3 and purified on a Mono Q column (Pharmacia) in accordance with procedures described by Becherer, J. D. and J. D. Lambris *Journal of Biological Chemistry* 1988 263:14586. C3c and C3d were generated by elastase treatment of C3 and purified on a Mono Q column as also described by Becherer and Lambris. Aggregated C3 was made using glutaraldehyde in accordance with procedures described by Erdei et al. *Eur. J. Immunol.* 1985 15:184. For iodination, native C3 was separated from C3($H_2$O) on a Mono S column and radiolabeled using $^{125}$I and Iodogen (Pierce Chemical Co., Rockford, Ill.). The specific activity of the labeled C3 varied from 1.0 to 2.5 µCi/µg.

Example 3

Construction of the Phage Library

The library consisted of 2×10$^8$ recombinants, each expressing the peptide sequence SR $X_{12}$ (S, P, T, or A) A (V, A, D, E, or G) $X_{12}$ SR, at the N-terminus of pIII. Fixed and semi-fixed amino acids (due to oligonucleotide design) are underlined. The library was constructed in accordance with procedures published by Kay et al. *Gene* 1993 128:59. The random amino acids were encoded by NNK, where N represents equimolar ratios of A, C, G, or T and K represents G or T. The NNK coding scheme utilizes 32 codons to encode 20 amino acids; the frequency of each amino acids is once (C, D, E, F, H, I, K, M, N, Q, W, Y), twice (A, G, P, V, T), or thrice (L, R, S) per codon.

Example 4

Biopanninq of the Phage Library

The C3-binding phage was isolated by screening the phage library described in Example 3. Microtiter well plates (Nunc Inc., Naperville, Ill.) were coated overnight with 20 µg of C3b in PBS at 4° C. and blocked with PBS containing 1% BSA for 30 minutes at 22° C. After washing, 6×10$^{11}$ plaque-forming units of the library were added to each well and incubated overnight at 4° C. The wells were washed five times with PBS containing 0.1% Tween 20 and 0.1% BSA. Bound phage particles were eluted with 100 mM glycine-HCl, pH 2.3, and immediately neutralized with 100 mM Tris-HCl, pH 8.5. Recovered phage particles were amplified in DH5αF' *E. coli*. This biopanning procedure was repeated twice. The amplified phage mixture obtained after the third round of amplification was plated, and positive phage were identified by confirming their binding to C3b in an ELISA, in which bound phage were detected by peroxidase-labeled anti-M13 antibody (Pharmacia). DNA was prepared from positive phage stocks and subjected to dideoxy sequencing in accordance with well known procedures.

Example 5

Synthesis and Purification of Peptides

Peptides were synthesized in an Applied Biosystem peptide synthesizer (model 431A) using Fmoc amide resin. The side chain protecting groups were: Cys(Trt), Asp(otBu), Arg (Pmc), Thr (tBu), Ser (tBu), Gln (Trt), Trp(Boc), His(Trt), Asn(Trt). Peptides were cleaved from the resin by incubation for 3 hours at 22 C. with a solvent mixture containing 5% phenol, 5% thioanisole, 5% water, 2.5% ethanedithiol, and 82.5% trifluoroacetic acid (TFA). The reaction mixture was filtered through a fritted funnel, precipitated with cold ether, dissolved in 50% acetonitrile containing 0.1% TFA, and lyophilized. The crude peptides obtained after cleavage were dissolved in 10% acetonitrile containing 0.1% TFA and purified using a reverse phase C-18 column (Waters, Milford, MA). Disulfide oxidation of purified peptides (SEQ ID NOs: 1, 2, 5–21) was performed by stirring a 0.15 mM solution of peptide in 0.1 M ammonium bicarbonate, pH 8.0, bubbling with oxygen at 22° C. for 48 hours. Purified peptides I were reduced with 10 mM dithiothreitol (DTT) and alkylated with 40 mM iodoacetamide. The identity and purity of all peptides were confirmed by laser desorption mass spectroscopy.

Example 6

Peptide Binding to C3 and C3 Fragments

Binding of synthetic peptide to C3 and to various fragments of C3 was evaluated by means of an ELISA. Microtiter plates (Nunc) were coated for 1 hour at 37° C. with 100 µl of peptide I (SEQ ID NO: 1) at 400 µg/ml or with 10 µg/ml of peptide I (SEQ ID NO: 2) coupled to BSA (1:1, w/w), then saturated with blocking buffer for 30 minutes at 22° C. The plates were washed three times with PBS containing 0.05% Tween 20, and various amounts of C3 or C3 fragments were added. After incubation for 1 hour at 22° C., the wells were washed and incubated at 22° C. for 1 hour with 100 µl of 2 µ/ml polyclonal rabbit anti-C3 antibody. Unbound anti-C3 antibodies were removed by washing, and a 1:1000 dilution of peroxidase-conjugated goat anti-rabbit IgG was added and incubated for 1 hour at 22 C. Color was developed by adding ABTS peroxidase substrate, and the optical density was read at 405 nm. Net binding was calculated by subtracting the readings obtained for nonspecific binding of C3 and C3 fragments to the plate in the absence of peptide.

Example 7

Hemolytic Assay

Inhibition of classical and alternative pathway activity by the peptides was measured. To determine the effect of peptides on the classical pathway, various concentrations of peptide were mixed with 11 µl of normal human serum (NHS, diluted 1:10 in GVB$^{++}$) and 5 µl of sheep erythrocytes coated with antibodies (EA) (1×10$^9$/ml) and GVB$^{++}$ was added to give a total volume of 250 µl. The reaction mixture was incubated at 37° C. for 1 hour and centrifuged. The percentage of lysis was determined by measuring the optical density of the supernatant at 414 nm. The effect of peptides on the alternative pathway was determined by measuring the lysis of rabbit erythrocytes (Er) in NHS. Various concentrations of peptide were mixed with 5 µl of NHS, 5 µl of MgEGTA and 10 µl of Er (1×10$^9$/ml) and brought to a final volume of 100 µl in GVB. The reaction mixture was incubated at 37° C. for 20 minutes and stopped by adding 200 µl of GVBE. After centrifugation, hemolysis was determined at 414 nm. The percentage of lysis was normalized by considering 100% lysis to be equal to the lysis occurring in the absence of the peptide.

Example 8

Measuremnt of C3 Convertase-mediated Cleavage of C3

Inhibition of C3 cleavage by peptide IV (SEQ ID NO: 2) in NHS was determined. Seven microliters of 35% NHS containing 0.5 µCi of $^{125}$I-C3 and 14.3 mM MgEGTA were mixed with graded concentrations of peptide IV (SEQ ID NO: 2) and 4 µl of 50% zymosan. The total volume of the reaction mixture was adjusted to 20 Al by adding GVB. Samples were incubated at 37° C. for 30 minutes, mixed with 10 µl of 30 mM EDTA, and centrifuged. The supernatant obtained was mixed with SDS sample buffer containing 10 mM DTT, analyzed on a 7.5% SDS-PAGE gel, and subjected to autoradiography. Radioactive bands were excised and counted to calculate the percentage of C3 cleaved. The percentage of $^{125}$I-C3 cleaved was normalized by considering 100% $^{125}$I-C3 cleaved to be equal to the $^{125}$I-C3 cleaved in the absence of the peptide. Controls were incubated in the presence of 10 mM EDTA.

The effect of peptide IV (SEQ ID NO: 2) on C3 cleavage by purified complement components was also determined. Two µg of C3 were incubated with various concentrations of the peptide at 37° C. for 15 minutes. Thereafter, 2 µg of factor B and 0.04 µg of factor D were added in the presence of 5 mM MgEGTA, in a total volume of 20 µl, to activate the pathway. After 2 hours at 37° C., samples were run on a 7.5% SDS-PAGE gel, stained, scanned for densitometric analysis, and the percentage of C3 cleaved was calculated. The data obtained were normalized by considering 100% C3 cleavage to be equal to the amount of C3 cleaved in the absence of the peptide. Controls were incubated in the presence of 10 mM EDTA.

Example 9

Measurement of Factor B Cleavage

The effect of peptide IV (SEQ ID NO: 2) on factor B cleavage was determined by quantitating the limited cleavage of factor B by factor D. C3b (2 µpg) was preincubated for 15 minutes at 37° C. with different concentrations of the peptide. The reaction mixture was then incubated at 37 C. for 30 minutes with 2 µpg of factor B and 0.06 ng of factor D in a total volume of 20 µl VBS containing 5 mM MgEGTA. The percentage of factor B cleaved was determined by electrophoresis of samples on a 7.5% SDS-PAGE gel under reducing conditions and densitometric analysis of the stained gel. Controls contained 10 mM EDTA instead of 5 mM MgEGTA.

Example 10

ELISA for Measurement of C3 Binding to Properdin

Binding of properdin to C3 was determined by ELISA. Microtiter wells were coated with 50 µl of C3 (20 µpg/ml) by incubation at 37° C. for 1 hour. After coating, wells were saturated with 200 µl of blocking buffer at 22° C. for 30 minutes and incubated 1 hour at 22° C. with 50 µl of NHS diluted 1:50 in PBS, pH 7.4, containing 10 mM EDTA. To determine the effect of peptide IV (SEQ ID NO: 2), various concentrations of the peptide were added to the reaction mixture. The amount of properdin bound to C3 was quantitated by adding 50 µl of polyclonal goat anti-properdin antibody (10 µg/ml), followed by 50 µl of peroxidase-conjugated anti-goat antibody diluted 1:1000 in PBS (BioRad, Hercules, Calif.). Each antibody was incubated at 37° C. for 1 hour and washed with PBS, pH 7.4 containing 0.05% Tween 20. Color was developed by adding ABTS peroxidase substrate, and optical density was measured at 405 nm.

Example 11

In Vivo Clearance of the C3-binding Peptide

A C3 binding peptide (C3BP) of the invention, containing tyrosine residues at its C-terminus (ICVVQDWGHHRCTAGHYY (SEQ ID NO: 23)), was labeled with $^{125}$I using Iodogen (Pierce) and purified on a reverse-phase C-8 cartridge (Waters). The labeled peptide had a specific activity of 0.7 µCi/µg. Normal SJL mice were injected via the tail vein with 1.4 µg of $^{125}$I-C3BP. Blood samples were withdrawn at various time intervals and the radioactivity was determined. The first sample, taken out immediately after injecting the labeled C3BP, is referred to as the zero time point.

Example 12

Retro-inverso Peptidomimetic of C3 Binding Peptide

Natural L peptides are vulnerable to cleavage by proteolytic enzymes in vivo. Therefore, solid-phase peptide synthesis methods were used to make a protease-resistant, retro-inverso peptidomimetic derivative of peptide of the invention (referred to herein as C3BP). In the synthesis of this analog, the direction of the sequence is reversed, changing the chirality of each amino acid by using all D-amino acid residues, thereby conferring protease resistance. Topographically, the D-amino acid side-chain configurations all correspond to the natural all L-form derivative, and activity may be preserved if the orientation of the side chain is the most important aspect of the specific ligand interaction system in question (Chorev, M. and Goodman, M. *Trends in Biotech.* 1993 13:438–445). Recent studies have demonstrated the preservation of the antigenicity of a retro-inverso peptide mimetic derivative of the C-terminus of a histone H3 sequence (Guichard et al. *Proc. Nat'l Acad. Sci. USA* 1994 91:9765–9769) and the transport function of a 16-mer retro-inverso form of a homeobox domain (Brugidou et al., *Biochem. Biophys. Res. Commun.* 1995 214:685–693). However, if instead the main-chain atoms play a significant role in the ligand interaction system, a retro-inverso peptidomimetic analog, along with its consequential change in directionality of the main chain atoms, may be inactive, as found in a recent study on a hormone-binding domain of a vasopressin receptor (Howl, J. and Wheatley, M. *Biochem. J.* 1996 317:577–582). The retro-inverso analog of the C3BP peptide was found to be inactive in the complement-mediated hemolytic assay, indicating that main chain atoms of the C3BP play a significant role in maintaining the preferred structure of the peptide.

The present invention is not limited to the embodiments specifically described and exemplified above, but is capable of variation and modification within the scope of the appended claims.

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
        (A) LENGTH: 27
        (B) TYPE: AMINO ACID
        (D) TOPOLOGY: LINEAR (xi) SEQUENCE DESCRIPTION: SEQ ID NO: 1:

ILE CYS VAL VAL GLN ASP TRP GLY HIS HIS ARG CYS THR ALA GLY
1               5                   10                  15

HIS MET ALA ASN LEU THR SER HIS ALA SER ALA ILE
                20                  25

(2) INFORMATION FOR SEQ ID NO: 2:

(i) SEQUENCE CHARACTERISTICS:
        (A) LENGTH: 13
        (B) TYPE: AMINO ACID
        (D) TOPOLOGY: LINEAR (xi) SEQUENCE DESCRIPTION: SEQ ID NO: 2:

ILE CYS VAL VAL GLN ASP TRP GLY HIS HIS ARG CYS THR
1               5                   10

(2) INFORMATION FOR SEQ ID NO: 3:

(i) SEQUENCE CHARACTERISTICS:
        (A) LENGTH: 17
        (B) TYPE: AMINO ACID
        (D) TOPOLOGY: LINEAR (xi) SEQUENCE DESCRIPTION: SEQ ID NO: 3:

ARG ALA THR ALA GLY HIS MET ALA ASN LEU THR SER HIS ALA SER
1               5                   10                  15

ALA ILE (2) INFORMATION FOR SEQ ID NO: 4:

(i) SEQUENCE CHARACTERISTICS:
        (A) LENGTH: 30
        (B) TYPE: AMINO ACID
        (D) TOPOLOGY: LINEAR (xi) SEQUENCE DESCRIPTION: SEQ ID NO: 4:

SER SER ILE CYS VAL VAL GLN ASP TRP GLY HIS HIS ARG CYS THR
1               5                   10                  15

ALA GLY HIS MET ALA ASN LEU THR SER HIS ALA SER ALA ILE ARG
                20                  25                  30

(2) INFORMATION FOR SEQ ID NO: 5:

(i) SEQUENCE CHARACTERISTICS:
        (A) LENGTH: 6
        (B) TYPE: AMINO ACID
        (D) TOPOLOGY: LINEAR (xi) SEQUENCE DESCRIPTION: SEQ ID NO: 5:

CYS HIS HIS ARG CYS THR
1               5

(2) INFORMATION FOR SEQ ID NO: 6:

(i) SEQUENCE CHARACTERISTICS:
        (A) LENGTH: 7
        (B) TYPE: AMINO ACID
        (D) TOPOLOGY: LINEAR (xi) SEQUENCE DESCRIPTION: SEQ ID NO: 6:

```
CYS GLY HIS HIS ARG CYS THR
1               5
```

(2) INFORMATION FOR SEQ ID NO: 7:

(i) SEQUENCE CHARACTERISTICS:
        (A) LENGTH: 8
        (B) TYPE: AMINO ACID
        (D) TOPOLOGY: LINEAR (xi) SEQUENCE DESCRIPTION: SEQ ID NO: 7:

```
CYS TRP GLY HIS HIS ARG CYS THR
1               5
```

(2) INFORMATION FOR SEQ ID NO: 8:

(i) SEQUENCE CHARACTERISTICS:
        (A) LENGTH: 9
        (B) TYPE: AMINO ACID
        (D) TOPOLOGY: LINEAR (xi) SEQUENCE DESCRIPTION: SEQ ID NO: 8:

```
CYS ASP TRP GLY HIS HIS ARG CYS THR
1               5
```

(2) INFORMATION FOR SEQ ID NO: 9:

(i) SEQUENCE CHARACTERISTICS:
        (A) LENGTH: 10
        (B) TYPE: AMINO ACID
        (D) TOPOLOGY: LINEAR (xi) SEQUENCE DESCRIPTION: SEQ ID NO: 9:

```
CYS GLN ASP TRP GLY HIS HIS ARG CYS THR
1               5                   10
```

(2) INFORMATION FOR SEQ ID NO: 10:

(i) SEQUENCE CHARACTERISTICS:
        (A) LENGTH: 11
        (B) TYPE: AMINO ACID
        (D) TOPOLOGY: LINEAR (xi) SEQUENCE DESCRIPTION: SEQ ID NO: 10:

```
CYS VAL GLN ASP TRP GLY HIS HIS ARG CYS THR
1               5                   10
```

(2) INFORMATION FOR SEQ ID NO: 11:

(i) SEQUENCE CHARACTERISTICS:
        (A) LENGTH: 7
        (B) TYPE: AMINO ACID
        (D) TOPOLOGY: LINEAR (xi) SEQUENCE DESCRIPTION: SEQ ID NO: 11:

```
CYS VAL VAL GLN ASP TRP CYS
1               5
```

(2) INFORMATION FOR SEQ ID NO: 12:

(i) SEQUENCE CHARACTERISTICS:
        (A) LENGTH: 9
        (B) TYPE: AMINO ACID
        (D) TOPOLOGY: LINEAR (xi) SEQUENCE DESCRIPTION: SEQ ID NO: 12:

```
CYS VAL VAL GLN ASP TRP GLY HIS CYS
1               5
```

(2) INFORMATION FOR SEQ ID NO: 13:

(i) SEQUENCE CHARACTERISTICS:
        (A) LENGTH: 11
        (B) TYPE: AMINO ACID
        (D) TOPOLOGY: LINEAR (xi) SEQUENCE DESCRIPTION: SEQ ID NO: 13:

```
CYS VAL VAL GLN ASP TRP GLY HIS HIS ARG CYS
1               5                   10
```

(2) INFORMATION FOR SEQ ID NO: 14:

(i) SEQUENCE CHARACTERISTICS:
        (A) LENGTH: 11
        (B) TYPE: AMINO ACID
        (D) TOPOLOGY: LINEAR (xi) SEQUENCE DESCRIPTION: SEQ ID NO: 14:

```
CYS ALA VAL GLN ASP TRP GLY HIS HIS ARG CYS
1               5                   10
```

(2) INFORMATION FOR SEQ ID NO: 15:

(i) SEQUENCE CHARACTERISTICS:
        (A) LENGTH: 11
        (B) TYPE: AMINO ACID
        (D) TOPOLOGY: LINEAR (xi) SEQUENCE DESCRIPTION: SEQ ID NO: 15:

```
CYS VAL ALA GLN ASP TRP GLY HIS HIS ARG CYS
1               5                   10
```

(2) INFORMATION FOR SEQ ID NO: 16:

(i) SEQUENCE CHARACTERISTICS:
        (A) LENGTH: 11
        (B) TYPE: AMINO ACID
        (D) TOPOLOGY: LINEAR (xi) SEQUENCE DESCRIPTION: SEQ ID NO: 16:

```
CYS VAL VAL ALA ASP TRP GLY HIS HIS ARG CYS
1               5                   10
```

(2) INFORMATION FOR SEQ ID NO: 17:

(i) SEQUENCE CHARACTERISTICS:
        (A) LENGTH: 11
        (B) TYPE: AMINO ACID
        (D) TOPOLOGY: LINEAR (xi) SEQUENCE DESCRIPTION: SEQ ID NO: 17:

```
CYS VAL VAL GLN ALA TRP GLY HIS HIS ARG CYS
1               5                   10
```

(2) INFORMATION FOR SEQ ID NO: 18:

(i) SEQUENCE CHARACTERISTICS:
        (A) LENGTH: 11
        (B) TYPE: AMINO ACID
        (D) TOPOLOGY: LINEAR (xi) SEQUENCE DESCRIPTION: SEQ ID NO: 18:

CYS VAL VAL GLN ASP ALA GLY HIS HIS ARG CYS
1               5                   10

(2) INFORMATION FOR SEQ ID NO: 19:

(i) SEQUENCE CHARACTERISTICS:
        (A) LENGTH: 11
        (B) TYPE: AMINO ACID
        (D) TOPOLOGY: LINEAR (xi) SEQUENCE DESCRIPTION: SEQ ID NO: 19:

CYS VAL VAL GLN ASP TRP ALA HIS HIS ARG CYS
1               5                   10

(2) INFORMATION FOR SEQ ID NO: 20:

(i) SEQUENCE CHARACTERISTICS:
        (A) LENGTH: 11
        (B) TYPE: AMINO ACID
        (D) TOPOLOGY: LINEAR (xi) SEQUENCE DESCRIPTION: SEQ ID NO: 20:

CYS VAL VAL GLN ASP TRP GLY ALA HIS ARG CYS
1               5                   10

(2) INFORMATION FOR SEQ ID NO: 21:

(i) SEQUENCE CHARACTERISTICS:
        (A) LENGTH: 11
        (B) TYPE: AMINO ACID
        (D) TOPOLOGY: LINEAR (xi) SEQUENCE DESCRIPTION: SEQ ID NO: 21:

CYS VAL VAL GLN ASP TRP GLY HIS ALA ARG CYS
1               5                   10

(2) INFORMATION FOR SEQ ID NO: 22:

(i) SEQUENCE CHARACTERISTICS:
        (A) LENGTH: 11
        (B) TYPE: AMINO ACID
        (D) TOPOLOGY: LINEAR (xi) SEQUENCE DESCRIPTION: SEQ ID NO: 22:

CYS VAL VAL GLN ASP TRP GLY HIS HIS ALA CYS
1               5                   10

(2) INFORMATION FOR SEQ ID NO: 23:

(i) SEQUENCE CHARACTERISTICS:
        (A) LENGTH: 18
        (B) TYPE: AMINO ACID
        (D) TOPOLOGY: LINEAR (xi) SEQUENCE DESCRIPTION: SEQ ID NO: 23:

ILE CYS VAL VAL GLN ASP TRP GLY HIS HIS ARG CYS THR ALA GLY
1               5                   10                  15

HIS TYR TYR

What is claimed is:

1. A cylclic peptide capable of inhibiting complement activation comprisuing the N-terminal cyclic region of a peptide of SEQ ID NO: 1 or comprising an amino acid sequence selected from the group consisting of SEQ ID NO: 2, SEQ ID NO: 13, SEQ ID NO: 15, SEQ ID NO: 20, SEQ ID NO: 21, and SEQ ID NO: 22.

2. A composition capable of inhibiting complement activation wherein said composition comprises the peptide of claim 1.

3. A method of inhibiting complement activation in an in vitro complement assay comprising addition of the peptide of claim 1 to assay.

4. A method of inhibiting complement activation that occurs during the use of artificial organs or implants comprising coating the surfaces of biomaterials used in an artificial organ or implant with the peptide of claim 1.

5. A method of inhibiting complement activation in a patient comprising administering to a patient the peptide of claim 1.

6. A method of treating complement-mediated tissue injury in a patient comprising administering to a patient an amount of the peptide of claim 1 effective to inhibit complement-activation in said patient.

7. A method of inhibiting complement activation during extracorporeal shunting of physiologic fluids comprising coating tubing through which said fluids flow with the peptide of claim 1.

* * * * *

UNITED STATES PATENT AND TRADEMARK OFFICE
CERTIFICATE OF CORRECTION

PATENT NO. : 6,319,897 B1
DATED : November 20, 2001
INVENTOR(S) : John D. Lambris et al.

It is certified that error appears in the above-identified patent and that said Letters Patent is hereby corrected as shown below:

Column 4,
Line 34, delete "Ag/ml" and insert -- $\mu$g/ml --.

Column 14,
Line 61, "Measuremnt" should be -- Measurement --.

Column 15,
Line 2, delete "Al" and insert -- $\mu$l --.
Line 32, delete "$\mu$pg" and insert -- $\mu$g --.
Line 35, delete "$\mu$pg" and insert -- $\mu$g --.
Line 49, delete "$\mu$pg/ml" and insert -- $\mu$g/ml --.

Column 25,
Line 3, change "comprisuing" to -- comprising --.

Signed and Sealed this

Ninth Day of April, 2002

JAMES E. ROGAN
*Director of the United States Patent and Trademark Office*